United States Patent
Gubitz et al.

(10) Patent No.: US 8,822,173 B2
(45) Date of Patent: Sep. 2, 2014

(54) WOUND DRESSING OR SWAB FOR DETECTING INFECTION

(71) Applicant: Eva Wehrschütz-Sigl, Graz (AT)

(72) Inventors: Georg Gubitz, Hart bei Graz (AT); Eva Wehrschütz-Sigl, Graz (AT); Andrea Hasmann, Graz (AT); Barbara Binder, Graz (AT); Michael Burnett, Tubingen (DE); Michael Schintler, Graz (AT)

(73) Assignee: Eva Wehrschutz-Sigl, Graz (AT)

( * ) Notice: Subject to any disclaimer, the term of this patent is extended or adjusted under 35 U.S.C. 154(b) by 0 days.

(21) Appl. No.: 13/943,009

(22) Filed: Jul. 16, 2013

(65) Prior Publication Data
US 2013/0337484 A1    Dec. 19, 2013

Related U.S. Application Data

(60) Division of application No. 13/299,067, filed on Nov. 17, 2011, now Pat. No. 8,497,085, which is a continuation of application No. PCT/EP2010/056811, filed on May 18, 2010.

(30) Foreign Application Priority Data

May 18, 2009  (EP) .................................... 09160557

(51) Int. Cl.
*C12Q 1/34* (2006.01)
(52) U.S. Cl.
USPC .................... 435/18; 435/23; 435/31; 435/34
(58) Field of Classification Search
USPC ......................................... 435/18, 23, 31, 34
See application file for complete search history.

(56) References Cited

U.S. PATENT DOCUMENTS

| | | | |
|---|---|---|---|
| 8,497,085 B2 * | 7/2013 | Gubitz et al. | 435/34 |
| 2004/0043422 A1 * | 3/2004 | Ferguson et al. | 435/7.1 |
| 2006/0240507 A1 | 10/2006 | Sanders et al. | |
| 2006/0292646 A1 * | 12/2006 | Colpas | 435/7.31 |
| 2007/0275423 A1 | 11/2007 | Sebastian et al. | |
| 2010/0215708 A1 * | 8/2010 | Zumbuehl et al. | 424/422 |
| 2011/0117025 A1 | 5/2011 | Dacosta et al. | |
| 2012/0135440 A1 | 5/2012 | Sanders et al. | |
| 2012/0282321 A1 * | 11/2012 | Cohen et al. | 424/445 |
| 2013/0098550 A1 * | 4/2013 | Sargeant et al. | 156/331.6 |

FOREIGN PATENT DOCUMENTS

| | | |
|---|---|---|
| EP | 0595846 A1 | 5/1994 |
| EP | 0864864 A1 | 9/1998 |
| GB | 2381452 A | 5/2003 |
| GB | 2418145 A | 3/2006 |
| GB | 2426335 A | 11/2006 |

OTHER PUBLICATIONS

Sommerhoff C. et al. Neutrophil Elastase and Cathepsin G Stimulate Secretion from Cultured Bovine Airway Gland Serous Cells J Clin Invest 85:682-689, Mar. 1990.
Choi Dong-Kug et al. Ablation of the inflammatory enzyme myeloperoxidase mitigates features of Parkinson's disease in mice. Jul. 2005. Journal of Neuroscience. vol. 25, No. 28, pp. 6594-6600.
International Search Report for PCT/EP2010/056811; Aug. 31, 2010.

* cited by examiner

*Primary Examiner* — Ralph Gitomer
(74) *Attorney, Agent, or Firm* — Edwards Wildman Palmer LLP; Ralph A. Loren; Christopher R. Cowles

(57) ABSTRACT

The present invention relates to a wound dressing or a wound swab, which allows the detection of at least three enzymes selected from the group consisting of lysosyme, elastase, cathepsin G and myeloperoxidase using colored substrate agents for these enzymes. These enzyme substrates can be bound to medically acceptable polymers or fibers.

8 Claims, No Drawings

WOUND DRESSING OR SWAB FOR DETECTING INFECTION

This application is a divisional of U.S. application Ser. No. 13/299,067, filed Nov. 17, 2011, issued as U.S. Pat. No. 8,497,085, which is the U.S. national phase, pursuant to 35 U.S.C. §371, of PCT/EP2010/056811 filed May 18, 2010, which claims the benefit of EP09160557.6 filed May 18, 2009. The contents of each application are incorporated by reference herein in their entirety.

The present invention relates to a method for detecting a wound infection.

Wound healing is the body's natural process of regenerating dermal and epidermal tissue. A set of complex cellular and biochemical events takes place in a closely orchestrated cascade to repair the damaged tissues, whereas the inflammatory, proliferative, and remodelling phases overlap in time. The coordinated actions of both resident and migratory cell populations within the extracellular matrix environment are essential for the restoration of anatomic continuity and function. Healing in acute wounds requires the coordinated completion of a variety of cellular activities including phagocytosis, chemotaxis, mitogenesis, collagen synthesis and the synthesis of other matrix components, and should be finished within 3 months.

As the wound healing process is very susceptible to interruption, various causes including infection, old age, diabetes and venous or arterial disease, are leading to the formation of chronic, non-healing wounds. In contrast to an acute wound, these chronic wounds fail to heal in a timely and orderly manner. Although chronic ulceration can affect any anatomical region, the most common site is the lower limb. The estimated prevalence of active leg ulceration in Europe is at least 0.1-0.3 percent. Ulcers secondary to venous hypertension and venous insufficiency account for nearly 70% of all leg ulcers, with diabetes and arterial disease contributing towards a significant proportion of the rest.

Wound healing in general is regulated by a multiplicity of bio molecules, including cytokines, growth factors and enzymes. In a chronic wound, the normal process of healing is disrupted at one or more points, mostly in the inflammatory or proliferative phases. Due to their importance in the healing process, alterations in the levels of growth factors or enzymes could account for the impaired healing observed in chronic wounds. In the phases of normal wound healing, the production and activity of proteases are tightly regulated. However, in chronic wound fluids, levels of various proteases including cathepsin G and neutrophil elastase, which is able to degrade fibronectin, an essential protein involved in the remodelling of the ECM, have also been observed to be significantly higher in chronic wounds. In addition, certain growth factors seem to be degraded by proteases, which are secreted mainly by macrophages and polymorphonuclear leucocytes.

Beside the imbalance of growth factors and enzymes, bacterial infection is a very common cause for chronic wounds. Since bacteria compete for nutrients and oxygen with macrophages and fibroblasts, bacterial infection can delay or even halt normal wound healing. Infection results when bacteria achieve dominance over the systemic and local factors of host resistance. This elicits a systemic septic response and also inhibits multiple processes involved in wound healing. Beside the relative number of micro-organisms and their pathogenicity, host response and factors such as immunodeficiency, diabetes mellitus and drugs, dictate whether a chronic wound becomes infected or shows signs of delayed healing. In addition to an increasing bacterial burden, biofilm formation and the presence of multidrug resistant organisms are detected in chronic wounds.

As infection does not only result in a prolonged inflammatory phase, but can cause further necrosis of the wound and can even lead to death as a consequence of sepsis, clinicians should be able to respond to infection rapidly. Current methods to identify bacterial infection rely mainly on judgement of the odour and appearance of the wound. By experts only (e.g. medical doctors), it is possible to identify infection in a wound by signs as redness, pain or bad odour.

In most cases, swabs are taken and micro-organisms are identified by cultivation. Results of this analysis are available only after 1-3 days. Additionally, as contamination and colonisation of wounds is quite normal, the information about the kind of species present in wounds is not a reliable indication for wound infection. Critical factors are: high levels of bacterial content, bacteria capable of altering their phenotypic and genotypic characteristics, presence of multi-drug resistant organisms and biofilm formation. Furthermore the virulence of pathogens is important, namely the production of endo- and exotoxins, which can be very harmful for the host. As the usage of swabs can only give information about the kind of bacteria and about the approximate number of the bacterial load, identification of bacterial species by microbiological methods or PCR is not a real diagnosis for infection. Furthermore, the method is expensive and takes at least three days.

If infection is suspected, blood tests very often provide an indication of following medical treatment. Beside the determination of the amount of white blood cells (leukocytes), the concentration of C—reactive protein (CRP) rises in case of infection. CRP belongs to the family of acute phase proteins and has a very short reaction time (12 hours). CRP-determinations have widely displaced the determination of erythrocyte sedimentation rate since it is less sensitive and has a time lag of more than one week. However, raised CRP levels are usually measured in blood which requires collection of blood and analysis in a clinical lab.

In summary, these available methods are time-consuming and cannot be used in home-care or for quick assessment during wound bandage changes. On the other hand, inspection of odour and appearance of the wound which could indicate infections requires experienced doctors.

Therefore there is a strong need for a fast prognostic aid for diagnosis of infection of a wound prior to obvious clinical symptoms of infection. Such a diagnostic tool would allow early intervention with suitable treatment and would reduce clinical intervention and the use of antibiotics. Also, such method should be simple and applicable in home care e.g. by nurses. These prerequisites require fast diagnosis in around 10 to 30 minutes. It is an object of the present invention to provide methods and means to satisfy the above identified need.

The present invention relates to a method for detecting a wound infection comprising the steps of:
  contacting a sample obtained from a wound with at least two substrates for at least two enzymes selected from the group consisting of lysozyme, elastase, cathepsin G and myeloperoxidase, and
  detecting a wound infection when a conversion of the at least two substrates with said at least two enzymes is determined and said conversion is increased (e.g. at least 50%, preferably at least 100%, more preferably at least 200%) compared to the conversion of said substrate in an uninfected wound.

Wounds which are infected by micro-organisms like bacteria or fungi contain specific enzymes in an increased amount compared to uninfected wounds. In particular the amount of the enzymes lysozyme, elastase, cathepsin G and myeloperoxidase is increased in infected wounds. An increased activity of one, preferably two, or all of said enzymes in a wound indicates an infection.

The present invention provides a method for a rapid and early diagnosis of wound infection. This so called "rapid diagnostic tool" is based on enzymes present in wound fluid which are associated with an inflammatory response of the human body. The application of appropriate substrates for enzymes, which are elevated in case of infection, may lead, for instance, to a colour reaction within minutes and allows a very fast estimation of the wound status. The invention comprises possible devices based on elevated levels of elastase, lysozyme, cathepsin G and myeloperoxidase as indicators for a possible wound infection.

Lysozyme (also known as Muramidase) is an enzyme comprising 129 amino acid residues with a molecular weight of approximately 14.7 kDa. Lysozyme is a component of cytoplasmic granules of the polymorphonuclear neutrophils (PMN) and the major secretory product of macrophages, found in mammalian secretions and tissues; and undoubtedly one of the principal important enzymes of our innate immune system. Due to the fact that the enzyme destroys bacterial cell walls by hydrolysis of 1,4-beta-linkages between N-acetyl-muramic acid and N-acetyl-D-glucosamine residues in peptidoglycan, it is commonly referred to as the "body's own antibiotic". In addition to its lytic activity against Gram positive bacteria, lysozyme can act as a non-specific innate opsonin by binding to the bacterial surface, reducing the negative charge and facilitating phagocytosis of the bacterium before opsonins from the acquired immune system arrive. Elevated levels of lysozyme in serum are described in case of some diseases; additionally elevated lysozyme levels could be detected in wound fluid samples in case of infection.

In humans, there exist two genes for elastase: Pancreatic elastase (ELA-1) and Neutrophil elastase (ELA-2). Neutrophil elastase (or leukocyte elastase LE: EC 3.4.21.37) is a 30-kD glycoprotein which belongs to the chymotrypsin family of serine proteases expressed by polymorphonuclear (PMN) leukocytes. The mature NE, a highly cationic glycoprotein, is targeted to primary granules where it is packaged with cathepsin G (another neutrophil serine protease).

Intracellular neutrophil elastase is a key effector molecule of the innate immune system, with potent antimicrobial activity against Gram-negative bacteria, spirochaetes, and fungi. Besides the involvement in control of pathogens by membrane degradation after internalization, catalytically active neutrophil elastase has been localized to the plasma membrane of mature neutrophils after release from intracellular stores. However, at inflammatory sites, neutrophil elastase is able to evade regulation, and once unregulated it can induce the release of pro-inflammatory cytokines, such as interleukin-6 and interleukin-8, leading to tissue destruction and inflammation that characterise numerous diseases. Elastin, which, together with collagen, determines the mechanical properties of connective tissue, has the unique property of elastic recoil, and plays a major structural function in lungs, arteries, skin and ligaments. Therefore, excess of LE activity has been involved in a number of pathological conditions leading to impairment of ECM organization, including rheumatoid arthritis, hereditary emphysema, chronic obstructive pulmonary disease, adult respiratory distress syndrome, ischemic-reperfusion injury emphysema, cystic fibrosis and tumor progression. Elevated elastase levels can be observed at the very beginning of infection and therefore the presence of elastase in wound fluid gives early stage warning of wound infection, before obvious clinical signs of infection are present.

Cathepsin G is a protease which belongs to the group of lysosomal cysteine proteases with a nucleophilic cysteine thiol in a catalytic triad. Together with human leucocyte elastase and proteinase 3, cathepsin G is a major content of the azurophil granules in neutrophils and is released at sites of inflammation.

Myeloperoxidase (MPO) is a 150 kDa peroxidase enzyme (EC 1.11.1.7) protein being existent as a dimer consisting of two 15 kDa light chains and two variable-weight glycosylated heavy chains bound to a prosthetic heme group This lysosomal protein is stored in azurophilic granules of the neutrophil. MPO produces hypochlorous acid (HOCl) from hydrogen peroxide ($H_2O_2$) and chloride anion (Cl—) during the neutrophil's respiratory burst. Hypochlorous acid and tyrosyl radical are cytotoxic and are able kill bacteria and other pathogens. While MPO deficiency killing is initially impaired but reaches normal levels after a period of time, suggesting that that an apparently slower, alternative mechanism of killing can take over in MPO-deficient neutrophils, elevated activity of MPO in case of infection was measured in blood and tissue. This seems to be due to the increased neutrophil infiltration to the infected site.

The invention is based on biochemical reactions causing colour changes due to the presence of four different enzymes in wounds at elevated levels in case of infection. The assessment of four different enzymes can compensate variations in the individual enzyme activities in wound fluids enhancing accuracy of the diagnostic tool.

In order to increase the accuracy of the method of the present invention the sample is preferably contacted with at least three, preferably at least four, of said substrates enabling the determination of the presence of at least three, preferably of all four, enzymes of the present invention.

The substrates used in the method of the present invention are specific for lysozyme, elastase, cathepsin G and/or myeloperoxidase. It is particularly preferred to use at least two of said enzyme-specific substrates in order to determine their increased presence in comparison to an uninfected wound. Preferred combinations of the substrates include substrates for lysozyme and elastase; cathepsin G and myeloperoxidase; lysozyme and cathepsin G; lysozyme and myeloperoxidase; elastase and cathepsin G; elastase and myeloperoxidase; lysozyme, elastase and cathepsin G; lysozyme, elastase and myeloperoxidase; lysozyme, cathepsin G and myeloperoxidase; elastase, cathepsin G and myeloperoxidase.

The sample obtained from the wound may be the wound fluid, a wound dressing comprising wound fluid or a swab comprising wound fluid.

The presence and the amount of the enzymes of the present invention in the wound can be determined by directly using the wound fluid. Alternatively wound dressings or swabs which have been contacted with the wound fluid may be used.

In order to determine the presence of lysozyme, elastase, cathepsin G and/or myeloperoxidase directly on a wound dressing or a swab, at least two substrates are preferably dispersed in a matrix of a medically acceptable polymer, preferably a hydrogel based on alginate, peptidoglycan and/or polygalacturonic acid, preferably provided in the form of e.g. a film or beads and/or bound to a fiber, in particular to a fiber of a wound dressing or a swab.

A particularly preferred wound dressing, swab or diagnostic stick may comprise a carrier, a biodegradable matrix e.g. mono-layer-or multilayer film or beads and a barrier. The carrier may be a polymer like polyamide or polypropylen. On said carrier a biodegradable matrix may be localized. This matrix may be elaborated for example as film (1-5 mm thickness) or beads as mono- or multilayer (2-8 mm in diameter).

The substrate of the enzymes, in particular of lysozyme and elastase, may be a polymer or biopolymer or dispersed in said polymers which can be degraded by said enzymes. For instance, a peptidoglycan polymer may act as a substrate for lysozyme and elastin as a substrate for elastase. The degradable polymer may comprise at least one substrate bound to at least one marker molecule like at least one dye which is released in the course of the substrate degradation. Multilayer films (e.g. at least 2, 3, 4, 5, 6, 7, 8, 9 or 10 layers) or beads may comprise a matrix containing the labeled enzyme substrate which is covered by non-labeled enzyme substrate. On the biodegradable polymer matrix a barrier layer is located. Said barrier layer is a non-degradable membrane which prevents that the substances of the biodegradable matrix and the substrate and converted substrates are released to the exterior. However, said barrier layer is permeable for the wound fluids.

According to a preferred embodiment of the present invention the substrate for lysozyme is selected from the group consisting of a dyed peptidoglycan, preferably a peptidoglycan of *Micrococcus lysodeictikus*, and dyed chitosan, both preferably dyed with a vinyl sulfone dye (e.g. Remazol).

The substrate for elastase is preferably selected from the group consisting of N-methoxysuccinyl-ala-ala-pro-val-p-nitroanilide and Cysteamid-Succ-Ala-Ala-Pro-Val-pNA, which is preferably directly bound to the carrier or to the matrix.

According to a further preferred embodiment of the present invention the substrate for cathepsin G is selected from the group consisting of N-methoxysuccinyl-ala-ala-pro-phe p-nitroanilide and Cysteamid-Succ-Ala-Ala-Pro-Phe-pNA, which is are preferably directly bound to the carrier or to the matrix.

According to a preferred embodiment of the present invention the substrate for myeloperoxidase is selected from the group consisting of 3,3',5,5'-tetramethylbenzidin, 2,2'-azino-bis(3-ethylbenzthiazoline-6-sulphonic acid), crystal violet, leuko crystal violet, sinaptic acid, alkoxysilanurea and other compounds like Fast Blue RR modified with isocyanat. The substrates may be covalently immobilized in the system. Hydrogen peroxide may be present as a co-substrate. The integration of cellobiose dehydrogenase (e.g. cellobiose dehydrogenase from *Myriococcum thermophilum*), desferri-oxamine mesylate and 5 to 500 mM, preferably 10 to 200 mM, in particular 30 mM, cellobiose as substrates, result in the production of hydrogen peroxide which is used by myeloperoxidase as a co-substrate. Of course also other enzyme systems involving other substrates may be used to produce hydrogen peroxide.

The amount of the substrates used may vary from substrate to substrate. Since the method of the present invention is optimized for a rapid detection of a wound infection the amount of substrate used depends on the conversion rate of the enzyme and on the environment (e.g. liquid, wound dressing, swab etc.) where the conversion occurs.

The amount of substrate and of wound fluid to be used varies further from the method of detection: fluid, in-gel (biodegradable matrix), swab, wound dressing etc.

In a liquid test system the amount of the elastase substrate added to a wound liquid sample having a volume in between 0.5 and 30 µl, preferably in between 1 and 15 µl, varies from 10 to 500 µl, preferably from 20 to 400 µl, more preferably from 50 to 300 µl, even more preferably from 80 to 150 µl, of a solution comprising 0.05 to 5 mM, preferably 0.05 to 2.5 mM, in particular 0.8 to 1.2 mM, substrate. In a particularly preferred embodiment of the present invention 4 to 6 µl, preferably 5 µl, of wound liquid is incubated with 90 to 110 µl, preferably 100 µl, of a substrate solution comprising 0.8 to 1.2 mM, preferably 1 mM, of elastase substrate, preferably N-methoxysuccinyl-ala-alapro-val-p-nitroanilide.

In a liquid test system the amount of the cathepsin G substrate added to a wound liquid sample having a volume in between 0.5 and 30 µl, preferably in between 1 and 15 µl, varies from 10 to 500 µl, preferably from 20 to 400 µl, more preferably from 50 to 300 µl, even more preferably from 80 to 150 µl, of a solution comprising 0.1 to 10 mM, preferably 0.5 to 5 mM, in particular 3 mM, substrate. In a particularly preferred embodiment of the present invention 4 to 6 µl, preferably 5 µl, of wound liquid is incubated with 90 to 110 µl, preferably 100 µl, of a substrate solution comprising 2 to 4 mM, preferably 3 mM, of cathepsin G substrate, preferably N-methoxysuccinyl-ala-ala-pro-phe p-nitroanilide.

In a liquid test system the amount of the myeloperoxidase substrate added to a wound liquid sample having a volume in between 0.5 and 30 µl, preferably in between 1 and 15 µl, varies from 10 to 500 µl, preferably from 20 to 400 µl, more preferably from 50 to 300 µl, even more preferably from 80 to 150 µl, of a solution comprising 0.01 to 1 mM, preferably 0.02 to 0.45 mM, substrate. In a particularly preferred embodiment of the present invention 4 to 6 µl, preferably 5 µl, of wound liquid diluted 1:10 to 1:30, preferably 1:20, is incubated with 90 to 110 µl, preferably 100 µl, of a substrate solution comprising 2 to 4 mM, preferably 3 mM, of myeloperoxidase substrate, preferably 3,3',5,5'-tetramethylbenzidin and/or 2,2'-azino-bis(3-ethylbenzthiazoline-6-sulphonic acid), crystal violet, 0.1 mm leuko crystal violet or natural phenolics like sinaptic acid, alkoxysilanurea and modified fast blue RR with isocyanate.

The solution comprising said substrates may further comprise 0.1 to 0.5 M, preferably 0.3 M, sucrose and 1 to 30 µl, preferably 15 µl $H_2O_2$. Instead of hydrogen peroxide, the system may contain an enzyme producing hydrogen peroxide from carbohydrates such as glucose oxidase or another carbohydrate oxidase such as cellobiohydrolase (CBH).

In a liquid test system the amount of the lysozyme substrate added to a wound liquid sample having a volume in between 0.5 and 30 µl, preferably in between 1 and 15 µl, varies from 1 to 25 mg, preferably from 5 to 20 mg, more preferably from 8 to 10 mg, in a solution comprising 1 to 30 ml, preferably 15 ml, buffer. In a particularly preferred embodiment of the present invention 4 to 6 µl, preferably 5 µl, of wound liquid is incubated with 90 to 110 µl, preferably 100 µl, of a substrate solution comprising lysozyme substrate, preferably a peptidoglycan, more preferably a peptidoglycan of *Micrococcus lysodeictikus*, and dyed chitosan, both preferably dyed with a vinyl sulfone dye (e.g. Remazol).

In a gel based test system for detecting elastase and cathepsin G activity 20 to 250 µl, preferably 50 to 150 µl, more preferably 100 µl of a 0.05 to 25 mM, preferably 0.1 to 20 mM, substrate solution are added to a 40 to 50° C., more preferably a 45° C., gel solution (comprising e.g. 1 to 2%, preferably 1.5% agarose) having a volume of 50 to 150 µl, preferably of 100 µl. To said gel a wound liquid sample having a volume in between 0.5 and 30 µl, preferably in between 1 and 15 µl, is added.

In a gel based test system for detecting myeloperoxidase activity a volume of 50 to 150 µl, preferably 100 µl, of a solution used for liquid testing is added to the same volume of heated gel as mentioned above. To said gel a wound liquid sample having a volume in between 0.5 and 30 µl, preferably in between 1 and 15 µl, is added.

In a gel based test system for detecting lysozyme activity 5 to 100 mg, preferably 10 to 75 mg, more preferably 15 to 50 mg, peptidoglycan, preferably of *Micrococcus lysodeictikus*, is suspended in a heated gel, preferably agarose gel (comprising e.g. 10 g agarose in a concentration of approx. 1% w/v). Alternatively the peptidoglycan is stained with a dye as described herein by heating peptidoglycan together with the dye to about 60 to 70° C. The precipitate can be used in testing lysozyme activity. Alternatively, the gel based test system comprises two layers of stained and unstained peptidoglycan. In case of Peptidoglycan degradation due to lysozyme activity, the colour would change from yellow to blue.

The swab based test systems are performed with the solutions as indicated above for the liquid based test systems. The swabs to be used are able to absorb 0.5 to 20 μl, preferably 1 to 15 μl, of wound fluid.

If the test system is used as an indicator on wound dressings the above mentioned solutions are brought on the dressing and dried or the enzymes substrates are bound covalently to the dressing.

Another aspect of the present invention relates to a wound dressing or swab comprising at least two substrates for at least two enzymes selected from the group consisting of lysozyme, elastase, cathepsin G and myeloperoxidase.

A wound dressing and a swab comprising said at least one substrate is particularly advantageous because it allows determining directly on said dressing and swab whether a wound is infected or not. The substrates to be used develop preferably a colour when converted by enzymes present in a sample to which said dressing or swab is contacted. Alternatively it is also possible to provide on the dressing or swab other substances capable to react with the converted substrate.

A wound dressing comprising said substrates and optionally means for detecting the conversion of the substrates by the enzymes present in an infected wound is particularly advantageous because it allows to monitor whether a wound covered by said dressing is infected or not. Consequently any person can decide when a wound dressing has to be changed.

The wound dressing or a diagnostic system, which may be positioned in the vicinity of a wound being in contact with the wound fluid may comprise a carrier layer, an operating matrix and a barrier layer. Enzymatically functionalised polyamide or polypropylenes can be used as carrier layers. For the operating matrix different blends of gels, e.g. alginate/agarose and gelatine, with incorporated enzyme substrates, such as peptidoglycan or chitosan as substrates for lysozyme, can be used. For instance, when the amount of lysozyme is determined combinations of agarose with various amounts of peptidoglycan ranging from 15 to 50 mg per 10 g agarose/gelatine may be applied. The barrier layer can be based on a membrane (with a thickness of e.g. 0.2 μm) to exclude converted substrate like coloured material from wound fluids such as erythrocytes. A clear response of this system to lysozyme and wound fluids can be obtained by measuring increased transparency at, e.g., 450 nm. Additionally, in case of high lysozyme activities, a release of the dye Remazol Brilliant Blue covalently bound to peptidoglycan could be detected by a colour change of the supernatant to blue, by a colour change of swab placed onto the system to blue or be measured at 600 nm.

According to a preferred embodiment of the present invention the dressing or swab comprises at least two, preferably at least three, in particular four, of said substrates.

According to a further preferred embodiment of the present invention the at least one substrate is dispersed in a matrix of a medically acceptable polymer or bound on a fiber.

The at least one substrate is preferably selected from the group consisting of a peptidoglycan, preferably a peptidoglycan of *Micrococcus lysodeictikus* dyed with a vinyl sulfone dye, N-methoxysuccinyl-ala-ala-pro-val-p-nitroanilide, N-methoxysuccinyl-ala-ala-pro-phe p-nitroanilide, 3,3',5,5'-tetramethylbenzidin, 2,2'-azino-bis(3-ethylbenzthiazoline-6-sulphonic acid), crystal violet, leuko crystal violet or other natural phenolics like sinaptic acid, alkoxysilanurea and Fast Blue RR modified with isocyanate.

The present invention is further illustrated in the following example, however, without being restricted thereto.

EXAMPLES

Example 1

Elastase Based Test—Liquid System

Preparation of Diagnostic System

100 μL of a solution of N-methoxysuccinyl-ala-ala-pro-val-p-nitroanilide dissolved at a concentration of 20 mM in DMSO in 0.1 M HEPES buffer (pH 7.4, containing 0.5 M NaCl) is pipetted into a transparent eppendorf tube. The final concentration of N-methoxysuccinyl-ala-ala-pro-val-p-nitroanilide can be between 0.05 to 2.50 mM, and is preferentially between 0.80 and 1.20 mM.

Diagnosis

A volume between 1 and 15 μL of wound fluid is added to the test system, preferentially between 4-6 μL and mixed by manual shaking for 10 seconds. This mixture is incubated at room temperature for 5 minutes. Thereafter, wound infection will be indicated by a colour change from light pink to yellow. Mixtures containing non infected wound samples will not change colour.

Test Protocol and Results:

5 μL of infected (A, B, C) and non infected wound samples (D, E, F) were incubated with the diagnostic system described in 1A containing a substrate concentration of 1.0 mM N-methoxysuccinyl-ala-ala-pro-val-p-nitroanilide. Visual inspection of the samples after 10 minutes of incubation indicated a colour change to yellow only for infected wound samples A, B, and C.

| Wound Sample | Infection according to diagnosis of medical doctors | Test response | Infection according to Test | Elastase activity* U/mL |
|---|---|---|---|---|
| A | yes | yellow | yes | 3.5 |
| B | yes | yellow | yes | 3.4 |
| C | yes | yellow | yes | 4.1 |
| D | no | no colour change | no | 0.4 |
| E | no | no colour change | no | 0.3 |
| F | no | no colour change | no | 0.4 |

*measured with N-methoxysuccinyl-ala-ala-pro-val-p-nitroanilide based standard assay Example 2

Elastase Based Test—Gel Based System

Preparation of Diagnostic System

N-methoxysuccinyl-ala-ala-pro-val-p-nitroanilide is dissolved at a concentration of 20 mM in dimethoxysulfoxide and diluted in 0.1 M HEPES buffer (pH 7.4, containing 0.5 M NaCl). The final concentration of N-methoxysuccinyl-ala-ala-pro-val-p-nitroanilide can be between 0.2 to 15 mM, and is preferentially between 0.50 and 5.00 mM. 100 μL of this solution is properly mixed with the equal volume of heated agarose (45° C.) solution (1.5% w/v) and transferred into wells of a 96 well plate.

Diagnosis

A volume between 1 and 15 μL of wound fluid is added to the test system, preferentially between 4-6 μL. This mixture is incubated at room temperature for 5 minutes. Thereafter, wound infection will be indicated by a colour change to yellow. Mixtures containing non infected wound samples will not change colour.

Test Protocol and Results:

5 μL of infected (A, B, C) and non infected wound samples (D, E, F) were incubated with the diagnostic system described 1B containing a substrate concentration of 5.0 mM N-methoxysuccinyl-ala-ala-pro-val-p-nitroanilide. Visual inspection of the samples after 10 minutes of incubation indicated a colour change to yellow only for infected wound samples A, B, and C.

| Wound Sample | Infection according to diagnosis of medical doctors | Test response | Infection according to Test |
|---|---|---|---|
| A | yes | yellow | yes |
| B | yes | yellow | yes |
| C | yes | yellow | yes |
| D | no | no colour change | no |
| E | no | no colour change | no |
| F | no | no colour change | no |

Example 3

Elastase Based Test—Swab Based System

Preparation of Diagnostic System

N-methoxysuccinyl-ala-ala-pro-val-p-nitroanilide is dissolved at a concentration of 20 mM in dimethoxysulfoxide and diluted in 0.1 M HEPES buffer (pH 7.4, containing 0.5 M NaCl). The final concentration of N-methoxysuccinyl-ala-ala-pro-val-p-nitroanilide can be between 0.2 to 10 mM, and is preferentially between 0.50 and 5.00 mM. 40 μL of this solution were pipetted into micro titre plates Diagnosis Small swabs (0.5×0.5 cm) of a polyester PES Microfibre (Microjet S1000) dipped into wound fluid thereby adsorbing between 1 and 12 μL of would liquid, preferentially between 5 and 8 μL. The test system is then placed into the microtiter plates containing the substrate solution and incubated at room temperature for 5 minutes. Thereafter, wound infection will be indicated by a colour change of the swab (i.e. polyester fabric) to yellow. Mixtures containing non infected wound samples will not change colour.

Test Protocol and Results:

Using small swabs (0.5×0.5 cm) of a polyester PES Microfibre (Microjet S1000) samples were taken from infected (A, B, C) and non infected wound samples (D, E, F) and placed into the diagnostic system described in 1C containing a substrate concentration of 1.0 mM N-methoxysuccinyl-ala-ala-pro-val-p-nitroanilide. Visual inspection of the samples after 10 minutes of incubation indicated a colour change to yellow only for infected wound samples A, B, and C.

| Wound Sample | Infection according to diagnosis of medical doctors | Test response | Infection according to Test |
|---|---|---|---|
| A | yes | yellow | yes |
| B | yes | yellow | yes |
| C | yes | yellow | yes |
| D | no | no colour change | no |
| E | no | no colour change | no |
| F | no | no colour change | no |

Example 4

Cathepsin Based Test—Liquid System

Preparation of Diagnostic System

N-succinyl-ala-ala-pro-phe-p-nitroanilide is dissolved at a concentration of 20 mM in dimethoxysulfoxide and diluted in 0.1 M HEPES buffer (pH 7.4, containing 0.5 M NaCl). The final concentration of N-methoxysuccinyl-ala-ala-pro-phe p-nitroanilide can be between 0.5 to 5 mM, and is preferentially 3 mM.

Diagnosis

A volume between 1 and 15 μL of wound fluid is added to the test system, preferentially between 4-6 μL and mixed by manual shaking. This mixture is incubated at 37° C. for 10 minutes. Thereafter, wound infection will be indicated by a colour change to yellow. Mixtures containing non infected wound samples will not change colour.

Test Protocol and Results:

5 μL of infected (A, B, C) and non infected wound samples (D, E, F) were incubated with the diagnostic system described in 1A comprising a substrate concentration of 3.0 mM N-methoxysuccinyl-ala-ala-pro-phe-p-nitroanilide. Visual inspection of the samples after 10 to 15 minutes of incubation indicated a colour change to yellow only for infected wound samples A, B, and C.

| Wound Sample | Infection according to diagnosis of medical doctors | Test response | Infection according to Test | Cathepsin G* U/mL |
|---|---|---|---|---|
| A | yes | yellow | yes | 40 |
| B | yes | yellow | yes | 36 |
| C | yes | yellow | yes | 45 |
| D | no | no colour change | no | 3 |
| E | no | no colour change | no | 2.5 |
| F | no | no colour change | no | 3.5 |

*measured with N-methoxysuccinyl-ala-ala-pro-phe-p-nitroanilide based standard assay Example 5

Cathepsin Based Test—Gel Based System

Preparation of Diagnostic System

N-methoxysuccinyl-ala-ala-pro-phe-p-nitroanilide is dissolved at a concentration of 20 mM in dimethoxysulfoxide and diluted in 0.1 M HEPES buffer (pH 7.4, containing 0.5 M NaCl). The final concentration of N-methoxysuccinyl-ala-ala-pro-phe-p-nitroanilide can be between 0.5 to 10 mM, and is preferentially 5.00 mM. 100 μL of this solution is properly mixed with the equal volume of heated agarose (45° C.) solution (1.5% w/v) and transferred into wells of a 96 well plate.

Diagnosis

A volume between 1 and 15 μL of wound fluid is added to the test system, preferentially between 4-6 μL. This mixture is incubated at 37° C. for 10 minutes. Thereafter, wound infection will be indicated by a colour change to yellow. Mixtures containing non infected wound samples will not change colour.

Test Protocol and Results:

5 μL of infected (A, B, C) and non infected wound samples (D, E, F) were incubated with the diagnostic system described in 1B containing a substrate concentration of 5.0 mM N-methoxysuccinyl-ala-ala-pro-phe-p-nitroanilide. Visual inspection of the samples after 10 minutes of incubation indicated a colour change to yellow only for infected wound samples A, B, and C.

| Wound Sample | Infection according to diagnosis of medical doctors | Test response | Infection according to Test |
|---|---|---|---|
| A | yes | yellow | yes |
| B | yes | yellow | yes |
| C | yes | yellow | yes |
| D | no | no colour change | no |
| E | no | no colour change | no |
| F | no | no colour change | no |

Example 6

Cathepsin Based Test—Swab Based System

Preparation of Diagnostic System

N-methoxysuccinyl-ala-ala-pro-phe-p-nitroanilide is dissolved at a concentration of 20 mM in dimethoxysulfoxide and diluted in 0.1 M HEPES buffer (pH 7.4, containing 0.5 M NaCl). The final concentration of N-methoxysuccinyl-ala-ala-pro-phe-p-nitroanilide can be between 0.5 to 10 mM, and is preferentially 5.00 mM. 40 μL of this solution were pipetted into micro titre plates Diagnosis Small swabs (0.5×0.5 cm) of a polyester PES Microfibre (Microjet S1000) dipped into wound fluid thereby adsorbing between 1 and 12 μL of would liquid, preferentially between 5 and 8 μL. The test system is then placed into the microtiter plates containing the substrate solution and incubated at 37° C. for 15 minutes. Thereafter, wound infection will be indicated by a colour change of the swab (i.e. polyester fabric) to yellow. Mixtures containing non infected wound samples will not change colour.

Test Protocol and Results

Using small swabs (0.5×0.5 cm) of a polyester PES Microfibre (Microjet S1000) samples were taken from infected (A, B, C) and non infected wound samples (D, E, F) and placed into the diagnostic system described in 1C containing a substrate concentration of 5.0 mM N-methoxysuccinyl-ala-ala-pro-phe-p-nitroanilide. Visual inspection of the samples after 15 minutes of incubation indicated a colour change to yellow only for infected wound samples A, B, and C.

| Wound Sample | Infection according to diagnosis of medical doctors | Test response | Infection according to Test |
|---|---|---|---|
| A | yes | yellow | yes |
| B | yes | yellow | yes |
| C | yes | yellow | yes |
| D | no | no colour change | no |
| E | no | no colour change | no |
| F | no | no colour change | no |

Example 7

Myeloperoxidase Based Test—Liquid System

Preparation of Diagnostic System

For this diagnostic tool, two different substrates can be used, namely TMB or ABTS. 3350 μl of succinate buffer (pH 5.4) comprising 0.3 M sucrose were used, 15 μl 1% $H_2O_2$ and 7 μl of the substrates (5-40 mM ABTS, 20-150 mM TMB, 0.0128 mM crystal violet and 0.025 mM of modified Fast Blue RR) were added. TMB (3,3',5,5'-Tetramethylbenzidine) is firstly dissolved in N,N-Methylformamide, crystal violet, leuko crystal violet and modified Fast Blue RR is dissolved in ethanol, while ABTS can be dissolved in water. 100 μl of the solutions are pipetted into a transparent eppendorf tube.

Diagnosis

A volume between 1 and 15 μL of wound fluid is added to the test system, preferentially between 4-6 μL and mixed by manual shaking for 10 seconds. This mixture is incubated at room temperature for 10 minutes. Thereafter, wound infection will be indicated by a colour change from colourless to blue (TMB or green (ABTS), respectively. Mixtures containing non infected wound samples will not change colour Test Protocol and Results:

Wound fluid of infected and uninfected samples is diluted 1:20. 5 μL of these dilutions of infected (A, B, C) and non infected wound samples (D, E, F) are incubated with the diagnostic system described in 1A containing the two different substrates. Visual inspection of the samples after 5 minutes of incubation indicated a colour change to blue in case of TMB only for infected wound samples A, B, and C.

| Wound Sample | Infection according to diagnosis of medical doctors | Test response | Infection according to Test | MPO activity* U/mL |
|---|---|---|---|---|
| A | yes | blue | yes | 190 |
| B | yes | blue | yes | 160 |
| C | yes | blue | yes | 175 |
| D | no | no colour change | no | 5 |
| E | no | no colour change | no | 12 |
| F | no | no colour change | no | 17 |

*measured with Guaiacol as based standard assay

Example 8

Myeloperoxidase Based Test—Gel System

Preparation of Diagnostic System

For this diagnostic tool, two different substrates can be used, namely TMB or ABTS. 3350 μl of succinate buffer (pH 5.4) comprising 0.3 M sucrose were used, 15 μl 1% $H_2O_2$ and 7 μl of the substrates (5-40 mM ABTS, 20-150 mM TMB, 0.0128 mM crystal violet, 0.1 mM leuko crystal violet or 0.025 mM of modified Fast Blue RR were added. TMB (3,3', 5,5'-Tetramethylbenzidine is firstly dissolved in N,N-Methylformamide, while ABTS can be dissolved in water. 100 μl of this solution is properly mixed with the equal volume of heated agarose (45° C.) solution (1.5% w/v) and transferred into wells of a 96 well plate.

Diagnosis

A volume between 1 and 15 μL of wound fluid is added to the test system, preferentially between 4-6 μL. This mixture is incubated at room temperature for 5 minutes. Thereafter, wound infection will be indicated by a colour change to blue and green, respectively. Mixtures containing non infected wound samples will not change colour.

Test Protocol and Results:

5 μL of infected (A, B, C) and non infected wound samples (D, E, F) were incubated with the diagnostic system described 1B containing the two substrates for MPO. Visual inspection of the samples after 5 minutes of incubation indicated a colour change to blue or green only for infected wound samples A, B, and C.

Example 9

Myeloperoxidase Based Test—Swab Based System

Preparation of Diagnostic System

3350 μl of succinate buffer (pH 5.4) comprising 0.3 M sucrose were used, 15 μl 1% $H_2O_2$ and 7 μl of the substrates (20 mM ABTS, 100 mM TMB, 0.0128 mM crystal violet, 0.1 mM leuko crystal violet and 0.025 mM of modified Fast Blue RR) were added. 40 μL of this solution were pipetted into micro titre plates.

Diagnosis

Small swabs (0.5×0.5 cm) of a polyester PES Microfibre (Microjet S1000) dipped into wound fluid diluted 1:20 thereby adsorbing between 1 and 12 μL of would liquid, preferentially between 5 and 8 μL. The test system is then placed into the microtiter plates containing the substrate solution and incubated at room temperature for 10 minutes. Thereafter, wound infection will be indicated by a colour change of the swab (i.e. polyester fabric) to blue or green, respectively. Mixtures containing non infected wound samples will not change colour.

Test Protocol and Results:

Using small swabs (0.5×0.5 cm) of a polyester PES Microfibre (Microjet S1000) samples were taken from infected (A, B, C) and non infected wound samples (D, E, F) diluted 1:20 and placed into the diagnostic system described in 1B containing the substrates TMB. Visual inspection of the samples after 5 minutes of incubation indicated a colour change to blue only for infected wound samples A, B, and C.

| Wound Sample | Infection according to diagnosis of medical doctors | Test response | Infection according to Test |
|---|---|---|---|
| A | yes | blue | yes |
| B | yes | blue | yes |
| C | yes | blue | yes |
| D | no | no colour change | no |
| E | no | no colour change | no |
| F | no | no colour change | no |

Example 10

Lysozyme Based Test—Liquid System

Preparation of Diagnostic System

An amount between 1 and 15 mg *Micrococcus lysodeikticus* peptidoglycan is suspended in 15 ml 0.1 M $KH_2PO_4$ buffer (pH 7.0). Preferentially, an amount between 8 and 10 mg is suspended. 290 μL of this solution is pipetted into a transparent eppendorf tube.

Diagnosis

A volume of 10 μL of wound fluid is added to the test system and mixed by manual shaking for 10 seconds. This mixture is incubated at 37° C. for 15 minutes. Thereafter, wound infection will be indicated by a decrease in turbidity. Mixtures containing non infected wound samples will not change.

Test Protocol and Results:

10 μL of infected (A, B, C) and non infected wound samples (D, E, F) were incubated with the diagnostic system described in 2A containing *Micrococcus lysodeikticus* as a substrate for lysozyme. Visual inspection of the samples after 15 minutes of incubation at 37° C. indicated a change of turbidity only for infected wound samples A, B, and C.

| Wound Sample | Infection according to diagnosis of medical doctors | Test response | Infection according to Test | lysozyme activity* U/mL |
|---|---|---|---|---|
| A | yes | clear | yes | 1200 |
| B | yes | clear | yes | 974 |
| C | yes | clear | yes | 1800 |
| D | no | turbid | no | 210 |
| E | no | turbid | no | 205 |
| F | no | turbid | no | 320 |

*measured with Micrococcus lysodeikticus peptidoglycan as a substrate

Example 11

Lysozyme Based Test—Gel Based System

Preparation of Diagnostic System 15 to 50 mg peptidoglycan of *Micrococcus lysodeictikus* is suspended in 10 g of agarose (1% w/v) which is dissolved in 0.1 M phosphate buffer pH 7.0 and heated in the microwave. The solution is properly mixed and transferred into wells of a 96 well plate. In a second assay, peptidoglycan (*Micrococcus lysodeictikus*) is stained with Remazol Brilliant Blue (RBB). Therefore, 50 mg peptidoglycan is suspended in 0.5 mL Remazol Brilliant Blue solution (0.5% w/v) and diluted with the equal volume of staining solution (2.5% w/v $NaSO_4$). Following thermal gradient is used: 25° C. for 10 minutes, 65° C. for 5 minutes. After centrifugation for 4 minutes at 13000 rpm, several washing steps are carried out until the supernatant is colourless. In a third assay, two layers of stained and unstained peptidoglycane are used, whereas the stained peptidoglycane is applied as described above (double layer system). Additionally, a matrix comprising 80% 1% agarose and 20% 2% gelatin, elastin, fibronectin and collagen respectively were used.

Diagnosis

A volume of 100 μL of wound fluid is added to the test system. This mixture is incubated at 37° C. between 15 and 60 minutes. Digestion of peptidoglycan due to lysozyme activity leads to an increase in transparency which can be measured at 450 nm and which can clearly be seen in case of infected wounds. In case of the dyed peptidoglycan, the dye is released into the supernatant, which turns to be blue in case of infected wounds. In case of the double layer system, the system changes colour from yellow to blue which can easily be seen after incubation for at least 30 minutes.

Test Protocol and Results:

100 μL of infected (A, B, C) and non infected wound samples (D, E, F) were incubated with the diagnostic system described 2B containing peptidoglycan as a substrate for lysozyme. Visual inspection of the samples after 15 and 60 minutes of incubation indicated a change in transparency only for infected wound samples A, B, and C.

| Wound Sample | Infection according to diagnosis of medical doctors | Test response Unstained system | Test response stained system | Test response Double layer system | Infection according to Test |
|---|---|---|---|---|---|
| A | yes | clear | Blue | Blue | yes |
| B | yes | clear | Blue | Blue | yes |
| C | yes | clear | Blue | Blue | yes |
| D | no | turbid | Clear | Yellow/white | no |
| E | no | turbid | Clear | Yellow/white | no |
| F | no | turbid | clear | Yellow/white | no |

Example 12

Lysozyme Based Test—Swab Based System

Preparation of Diagnostic System 15 to 50 mg peptidoglycan of *Micrococcus lysodeictikus* dyed with Remazol Brilliant Blue (RBB) is suspended in 10 g of agarose (1% w/v) dissolved in 0.1 M phosphate buffer pH 7.0 and heated in the microwave. The solution is properly mixed and transferred into wells of a 96 well plate.

Diagnosis

Small swabs (0.5×0.5 cm) of a polyester PES Microfibre (Microjet S1000) are dipped into wound fluid thereby adsorbing between 1 and 12 µL of wound liquid, preferentially between 5 and 8 µL. The swab is then rinsed in buffer solution and this solution is then placed into the microtiter plates containing the gel based system with dyed peptidoglycan. The system is then incubated at 37° C. for 30 minutes. Thereafter, wound infection will be indicated by a blue supernatant/the fabrics turning blue in case of infected wounds.

Test Protocol and Results:

Using small swabs (0.5×0.5 cm) of a polyester PES Microfibre (Microjet S1000) samples were taken from infected (A, B, C) and non infected wound samples (D, E, F) and placed into the diagnostic system described above containing the gel based system with remazol dyed peptidoglycan. Visual inspection of the supernatant/the fabrics after 30 minutes of incubation indicated the development of a blue colour only for infected wound samples A, B, and C.

Example 13

Combination of Enzymes—Liquid System

Preparation of Diagnostic System

100 µl of the liquid substrates described for the enzymes elastase, myeloperoxidase and Cathepsin G (see examples 1 to 10) were prepared and transferred to a microtiter plate.

Diagnosis

5 µl of wound fluids from infected wounds (A-F) and non infected wounds (G-L) are added. Wound fluid can be taken with a capillary or a syringe and is aliquoted afterwards. Alternatively, swabs were used to transfer samples from infected wounds (A-F) and non infected wounds (G-L) to 1-2 ml of buffer solution. Aliquots of 250 ul (500 µl) were added to the microtiter plate with the four different enzyme substrates.

Plates are incubated at 37° C. After 10 minutes, the assay for elastase was inspected and turned to yellow in case of the infected wounds. After 30 minutes the Cathepsin G and the lysozyme assay were inspected and indicated infection by turning to yellow, blue and clear, respectively. After 5 minutes, two assays for MPO (TMB and ABTS) were inspected and indicated infection by turning to blue and green respectively. After 60 minutes, the assay for MPO using crystal violet, leuko crystal violet and modified Fast Blue RR was inspected and indicated infection by changing the colour.

Sample A shows a less pronounced colour development in the Elastase assay, but was clearly positive in the other assays. In contrast, samples D and E show a less pronounced colour development in the MPO ABTS assay while they were positive in the other assays. This confirms the importance of the combination of at least 2, preferably 3, most preferably 4, different assays for the diagnostic tool.

We claim:

1. A wound dressing or swab comprising a substrate for lysozyme plus at least two different substrates for at least two different enzymes selected from the group consisting of elastase, cathepsin G and myeloperoxidase, wherein said substrates are capable of releasing a colored agent.

2. The wound dressing or swab according to claim 1, wherein the wound dressing or swab comprises at least four of said substrates.

3. The wound dressing or swab according to claim 1, wherein at least one of said substrates is dispersed or covalently bound in a matrix of a medically acceptable polymer.

4. The wound dressing or swab according to claim 3, wherein said medically acceptable polymer is a hydrogel.

5. The wound dressing or swab according to claim 1, wherein at least one of said substrates is bound on a fiber.

6. The wound dressing according to claim 5, wherein said fiber is selected from the group consisting of a fiber of the wound dressing and a fiber of the swab.

7. The wound dressing according to claim 1, wherein at least three substrates are selected from the group consisting of a peptidoglycan, N-methoxysuccinyl-ala-ala-pro-val-p-nitroanilide, N-methoxysuccinyl-ala-ala-pro-phe p-nitroanilide, 3,3',5,5'-tetramethylbenzidin, 2,2'-azino-bis(3-ethylbenzthiazoline-6-sulphonic acid), crystal violet, leuko crystal violet and sinaptic acid Fast Blue RR modified with Isocynat.

8. The wound dressing according to claim 7, wherein said peptidoglycan is a peptidoglycan of *Micrococcus lysodeictikus* dyed with a vinyl sulfone dye.

* * * * *